(12) United States Patent
Lothschuetz et al.

(10) Patent No.: US 9,303,054 B2
(45) Date of Patent: Apr. 5, 2016

(54) PROCESS FOR THE DIASTEREOSELECTIVE PREPARATION OF RUTHENIUM COMPLEXES

(71) Applicant: Syngenta Participations AG, Basel (CH)

(72) Inventors: Christian Lothschuetz, Munchwilen (CH); Alexandre Christian Saint-Dizier, Munchwilen (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/781,980

(22) PCT Filed: Apr. 1, 2014

(86) PCT No.: PCT/EP2014/056495
§ 371 (c)(1),
(2) Date: Oct. 2, 2015

(87) PCT Pub. No.: WO2014/166777
PCT Pub. Date: Oct. 16, 2014

(65) Prior Publication Data
US 2016/0046658 A1   Feb. 18, 2016

(30) Foreign Application Priority Data

Apr. 8, 2013 (EP) ..................... 13162679

(51) Int. Cl.
*C07F 15/00* (2006.01)
*B01J 31/24* (2006.01)

(52) U.S. Cl.
CPC ......... *C07F 15/0053* (2013.01); *B01J 31/2409* (2013.01); *B01J 2231/643* (2013.01); *B01J 2531/821* (2013.01)

(58) Field of Classification Search
USPC ....................................... 546/10, 2
See application file for complete search history.

(56) References Cited

FOREIGN PATENT DOCUMENTS

WO    2005105819 A1    11/2005

OTHER PUBLICATIONS

Baratta et al, "2-(Aminomethyl)pyridine-Phosphine Ruthenium (II) Complexes: Novel Highly Active Transfer Hydrogenation Catalysts"; Organometallics 2005, 24:1660-1669.
Carpenter et al, "Convenient and improved protocols for the hydrogenation of esters using Ru catalysts derived from (P,P), (P,N,N) and (P,N,O) ligands"; Dalton Transactions 2012, 41:10136-10140.
International Search Report for International Patent Application No. PCT/2014/056495 mailed Apr. 29, 2014.

*Primary Examiner* — Charanjit Aulakh
(74) *Attorney, Agent, or Firm* — R. Kody Jones

(57) ABSTRACT

The present invention relates to a process for the preparation of a compound of formula (I), wherein X is $—CH_2—$, $—CH_2—CH_2—$, $—CH_2—CH_2—CH_2—$ or $—CH_2—CH_2—CH_2—CH_2—$; $Y_1$ is $—CH_2—$; $—CH_2—CH_2—$ or $—NH—$; $Y_2$ is $NHR_7$ or SH; wherein $R_7$ is hydrogen, $C_1$-$C_4$alkyl or phenyl; $R_{-1}$ and $R_2$, independently from each other, represent aliphatic or aromatic groups; $R_3$ and $R_4$, independently from each other, represent aliphatic or aromatic groups; $R_5$ and $R_6$ are each hydrogen or represent together with the carbon atoms to which they are bonded, a phenyl ring; which process comprises reacting a compound of formula II [$RuCl_2(R_8)$n]m (II), wherein n is 1 and m is >1 which represents a polymeric structure if $R_8$ is a molecule containing two alkene or alkyne moieties coordinating in an hapto-2 coordination mode to the metal; or n is 4 and m is 1 if $R_8$ is a nitrogen, oxygen or sulfur containing molecule in which said nitrogen, oxygen or sulfur coordinate to the metal; in the presence of an inert solvent which boiling point is from 1 12° C. to 165° C. with a compound of formula (III), wherein $R_5$, $R_6$, $Y_1$ and $Y_2$ are as defined under formula I, and a phosphane of formula IV $R_3R_4P—X—PR_1R_2$ (iv), wherein $R_1$, $R_2$, $R_3$, $R_4$ and X are as defined under formula I.

8 Claims, No Drawings

PROCESS FOR THE DIASTEREOSELECTIVE PREPARATION OF RUTHENIUM COMPLEXES

RELATED APPLICATION INFORMATION

This application is a 371 of International Application No. PCT/EP2014/056495, filed 1 Apr. 2014, which claims priority to EP Patent Application No. 13162679.8 filed 8 Apr. 2013, the contents of which are incorporated herein by reference herein.

The present invention relates to a process for the diastereoselective preparation of ruthenium complexes and their use as catalysts in the hydrogenation of C=N and C=O double bonds and in the oxidative synthesis of amides or esters.

It is known that the cis-form of certain ruthenium(II) complexes, for example $RuCl_2[PPh_2(CH_2)_4PPh_2][2-(H_2NCH_2)C_5H_4N]$ of formula Ia

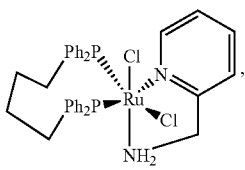

are useful as a highly active hydrogenation catalysts. Said complex, its preparation and use as catalyst is described, for example, in WO 2005/105819 and in Crabtree et al. *Organometallics* 2011, 30, 4174-4179. The catalyst can either adopt a cis or a trans configuration with respect to the chloro ligands. The cis-form of this complex is especially preferred since it shows much higher reactivity in the above mentioned hydrogenation reactions (Baratta et al., *Organometallics* 2005, 24, 1660-1669). It is therefore highly desired to selectively prepare the cis-form of said complex.

Clarke and co-workers report a procedure delivering structurally related complexes by consecutive addition of the ligands to the precursor [RuCl2(Py)2(NBD)] in methyl-THF (Clarke et al. Dalton Trans. 2012, 41, 10136). However, the boiling point of methyl-THF is not sufficiently high to allow the formation of the highly active cis-complexes (the steric rearrangement needs high reaction temperatures e.g. boiling toluene). Another significant disadvantage of their procedure is the used catalyst precursor which is highly expensive and not available on an industrial scale. Further, the procedure reported by Clarke and co-workers includes the generation of two equivalents of toxic pyridine.

The synthesis of the compound of formula Ia according to WO 2005/105819, Crabtree et al. *Organometallics* 2011, 30, 4174-4179 and Baratta et al., *Organometallics* 2005, 24, 1660-1669 is based on a two step procedure. Further, long reaction times (20 hours) are described in preparatory examples 5 and 6 of WO 2005/105819. Moreover, all these procedures start from a catalyst precursor containing triphenlyphosphine as ligand. Said catalyst precursor has the formula $RuCl_2(PPh_3)n$ (with n=3.0, 3.1, 3.2, 3.3, 3.4, 3.5, 3.6, 3.7, 3.8, 3.9 and 4.0) (Caulton et al., *J. Am. Chem. Soc.* 1975, 4221-4228). It can be derived from the formula of said catalyst precursor that it contains a large amount of triphenlyphosphine ligand that has to be exchanged in the next step. From an economical and environmental point of view this exchange is highly problematic as at least three equivalents of phosphorous waste are generated per equivalent of catalyst.

The aim of the present invention is therefore to provide a novel, robust process for the diastereoselective production of the cis-form of $RuCl_2$ complexes of formula I in high yields and good quality in an economically advantageous way.

Thus, according to the present invention, there is provided a process for the preparation of a compound of formula I

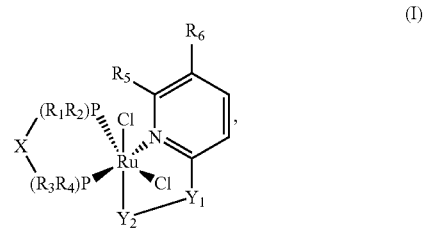

wherein
X is $-CH_2-$, $-CH_2-CH_2-$, $-CH_2-CH_2-CH_2-$ or $-CH_2-CH_2-CH_2-CH_2-$;
$Y_1$ is $-CH_2-$; $-CH_2-CH_2-$ or $-NH-$;
$Y_2$ is $NHR_7$ or SH; wherein $R_7$ is hydrogen, $C_1$-$C_4$alkyl or phenyl;
$R_1$ and $R_2$, independently from each other, represent aliphatic or aromatic groups;
$R_3$ and $R_4$, independently from each other, represent aliphatic or aromatic groups;
$R_5$ and $R_6$ are each hydrogen or together represent with the carbon atoms to which they are bonded, a phenyl ring; which process comprises reacting a compound of formula II

wherein n is 1 and m is >1 which represents a polymeric structure if $R_8$ is a molecule containing two alkene or alkyne moieties coordinating in an hapto-2 coordination mode to the metal;
or n is 4 and m is 1 if $R_8$ is a nitrogen, oxygen or sulfur containing molecule in which said nitrogen, oxygen or sulfur coordinate to the metal;
in the presence of an inert solvent which boiling point is from 112° C. to 165° C. with a compound of formula III

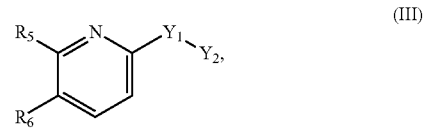

wherein $R_5$, $R_6$, $Y_1$ and $Y_2$ are as defined under formula I, and a phosphane of formula IV

wherein $R_1$, $R_2$, $R_3$, $R_4$ and X are as defined under formula I.
In a preferred embodiment of the invention,
X is preferably $-CH_2-CH_2-CH_2-CH_2-$.
In said preferred embodiment of the invention,
$R_8$ is preferably cis,cis-cycloocta-1,5diene (cyclooctadiene or abbreviated as COD) or bicyclo[2.2.1]hepta-2,5-diene (norbornadiene or abbreviated as NBD) if n is 1 and m >1; or is preferably dimethylsulfoxide resulting in $RuCl_2(dmso-κO RuCl_2(dmso-κS)_3(dmso-κO)$ or $RuCl_2(dmso-κS)_4$ as precursors if n is 4 and m is 1, but in particular cis,cis-cycloocta-1,5diene or bicyclo[2.2.1]hepta-2,5-diene.

In said preferred embodiment of the invention,
$R_1$, $R_2$, $R_3$ and $R_4$ are preferably phenyl and
$R_5$ and $R_6$ are preferably hydrogen or together represent with the carbon atoms to which they are bonded, a phenyl ring;
$Y_1$ is preferably —$CH_2$—, and
$Y_2$ is preferably $NH_2$.

The boiling point of the inert solvent according to the process of the invention is given at an atmospheric pressure of 1023.25 hPa. To achieve economically favourable reaction times, the reaction is performed at temperatures above 112° C. (temperature at a pressure of 1023.25 hPa). Preferred inert solvents are ketones, preferably cyclohexanone, esters, preferably ethyl butyrate and aromatic solvents or mixtures of aromatic solvents with a boiling point from 112° C. to 165° C. (temperature at a pressure of 1023.25 hPa), preferably xylene and halogenated aromatic compounds preferably chlorobenzene.

In said preferred embodiment of the invention, the inert solvent is preferably cyclohexanone, ethyl butyrate, xylene or chlorobenzene.

Preferred compounds of formula III for the process according to the invention are selected from the group consisting of the formulae

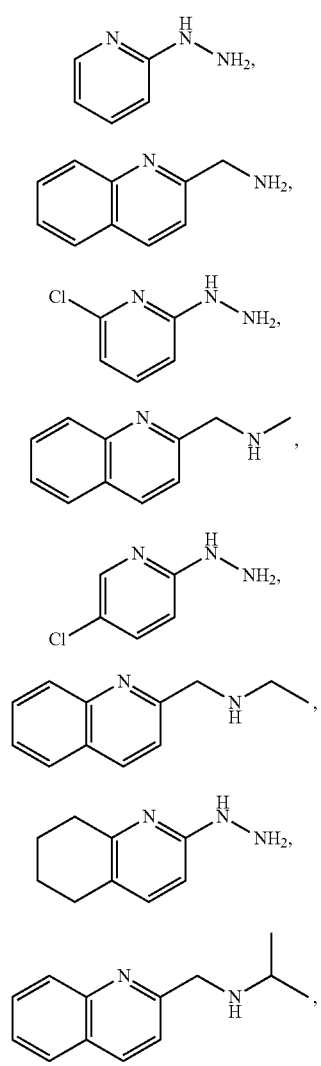

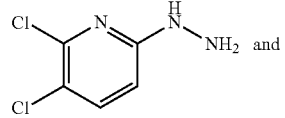

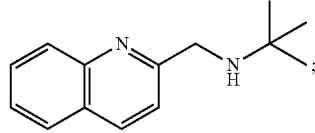

wherein the radicals signify methyl groups. The use of said preferred compounds of formula III-1 to III-10 are also especially preferred in said preferred embodiment of the invention mentioned above.

A preferred embodiment of the process according to the invention is characterized by reacting a compound of formula IIa

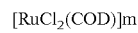

wherein (m is >1);
with 1.225 equivalents of a bidentate amine ligand preferably 2-picolylamine or the compound (III-2) in presence of 1 equivalent of a bidentate phosphine ligand preferably 1,4-bis (diphenylphosphino)butane in an inert solvent like cyclohexanone at a reaction temperature from 125 to 135° C.

The process according to the present invention is especially useful for the preparation of catalysts of the formulae Ia and Ib

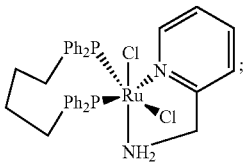

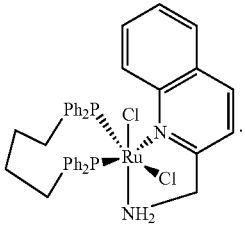

The catalyst of the formula Ib is novel and represent a further object of the invention. The catalyst of the formula Ib crystallize more rapidly during subsequent purification; thereby enabling faster filtration times and lower residual catalyst in the substrate solution. This is in particular of importance for the large scale production of the catalyst.

The process is preferably performed as an one pot procedure. An advantage of the one pot procedure in particular for large-scale manufacturing are significantly reduced reaction times. In addition, phosphane containing waste is remarkably reduced compared to the prior art process described in WO 2005/105819.

The synthesis of the precursors can be accomplished by a person skilled in the art following the procedures described in Albers et. al. *Inorg. Synth.* 1989, 26, 68-77 for $RuCl_2$(cyclooctanediene) and Albers et. al. *Inorg. Synth* 1989, 26, 249-258 for $RuCl_2$(bicyclo[2.2.1]hepta-2,5-diene) or Castellano et. al. *Inorg. Chim. Acta.* 2009, 363, 283-287 for [$RuCl_2$ (dmso-κS)$_3$(dmso-κO)] as well as Riant et. al. *Chem. Eur. J.* 2009, 15, 6267-6268) for RuCl$_2$(dmso-κS)$_4$.

The catalyst precursors RuCl$_2$(cyclooctanediene) and RuCl$_2$(bicyclo[2.2.1]hepta-2,5-diene) show polymeric structures (illustrated by the definition m>1). In these cases the molecular formulae are more exactly represented by [RuCl$_2$(cyclooctanediene)]$_m$ and [RuCl$_2$(bicyclo[2.2.1]hepta-2,5-diene)]$_m$. with m>1. This fact is also described in the above mentioned literature citations.

Preferably precursors with highest metal content and purities are used
typically 29-37 weight-% ruthenium for [RuCl$_2$(cyclooctanediene)]$_m$,
31-39 weight-% ruthenium for [RuCl$_2$(bicyclo[2.2.1]hepta-2,5-diene)]$_m$ and
16-21 weight-% ruthenium for [RuCl$_2$(dmso-κS)$_3$(dmso-κO)] and for RuCl$_2$(dmso-κS)$_4$.

The efficiency of the catalysts of formula Ia made from [RuCl$_2$(COD)]$_m$ as the precursor is equivalent to that of the catalyst of formula Ia made from [RuCl$_2$(PPh$_3$)$_n$] as the precursor for both reduction under hydrogen atmosphere and transfer hydrogenation.

TABLE 1

Catalytic reduction of acetophenone to 1-phenylethanol under hydrogen atmosphere in the presence of ruthenium complexes

| Pre-catalyst | Molar ratio Acetophenone/ Ru/Base | Pressure bar | Conversion % | Reaction Time min |
|---|---|---|---|---|
| [RuCl$_2$(PPh$_3$)$_n$] | 4000/1/85 | 9 | 99 | 225 |
| [RuCl$_2$(COD)]$_m$ | 4000/1/85 | 9 | 99 | 225 |

TABLE 2

Catalytic reduction of acetophenone to 1-phenylethanol in the presence of ruthenium complexes

| Pre-catalyst | Molar ratio Acetophenone/ Ru/Base | Conversion % | Reaction Time min |
|---|---|---|---|
| [RuCl$_2$(PPh$_3$)$_n$] | 4000/1/85 | 98 | 30 |
| [RuCl$_2$(COD)]$_m$ | 4000/1/85 | 94 | 60 |

PREPARATORY EXAMPLES

Example P1

Preparation of RuCl$_2$[PPh$_2$(CH$_2$)$_4$PPh$_2$][2-H$_2$NCH$_2$)C$_5$H$_4$N] of formula Ia

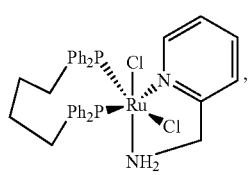

(Ia)

The catalyst precursor, preferably [RuCl$_2$(COD)]m (1 eq.) (COD=cis,cis-cycloocta-1,5diene), 1,4-bis(diphenylphosphino)butane (1.0-1.2 eq., preferably 1.0 eq.) and 2-picolylamine (1.0-1.4 eq., preferably 1.225 eq.) were dissolved in one of the above mentioned solvents, preferably methyl isobutylketone (10-20 ml/g Ru-precursor, preferably 20 ml/g). The mixture was heated to reflux for 3-5 hours and then cooled to ambient temperature. The solid precipitate was filtered off and washed with the same solvent that was used for the reaction. A person skilled in the art can determine the cis-/trans-isomeric ratio by NMR. The diastereomeric ratios generated by this method are usually in the range of d.r. (diastereomeric ratio) >98% towards the cis isomer. The same results can be achieved starting with [RuCl$_2$(dmso-κS)$_3$(dmso-κO)], [RuCl$_2$(dmso-κS)$_4$] or [RuCl$_2$(bicyclo[2.2.1]hepta-2,5-diene]$_m$ as precursor.

Example P2

Preparation of RuCl$_2$[PPh$_2$(CH$_2$)$_4$PPh$_2$][2-H$_2$NCH$_2$)C$_9$H$_6$N] of formula Ib

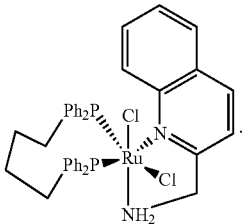

(Ib)

The catalyst precursor, preferably [RuCl$_2$(COD)]m (1 eq.), 1,4-bis(diphenylphosphino)butane (1.0-1.2 eq., preferably 1.0 eq.) and 2-quinolinylmethylamine (1.0-1.4 eq., preferably 1.225 eq.) were dissolved in one of the above mentioned solvents, preferably cyclohexanone (10-20 ml/g Ru-precursor, preferably 20 ml/g). The mixture was heated at 130° C. for 1 hour and then cooled to ambient temperature. The solid precipitate was filtered off and washed with the same solvent that was used for the reaction. A person skilled in the art can determine the cis-/trans-isomeric ratio by NMR. The diastereomeric ratios generated by this method are usually in the range of d.r. (diastereomeric ratio) >98% towards the cis isomer. The same results can be achieved starting with [RuCl$_2$(dmso-κS)$_3$(dmso-κO)], [RuCl$_2$(dmso-κS)$_4$] or [RuCl$_2$(bicyclo[2.2.1]hepta-2,5-diene)]$_m$ as precursor.

What is claimed is:
1. A process for the preparation of a compound of formula I

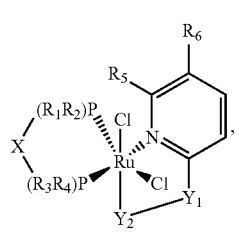

(I)

wherein
X is —CH$_2$—, —CH$_2$—CH$_2$—, —CH$_2$—CH$_2$—CH$_2$— or —CH$_2$—CH$_2$—CH$_2$—CH$_2$—;
Y$_1$ is —CH$_2$—; —CH$_2$—CH$_2$— or —NH—;

Y$_2$ is NHR$_7$ or SH; wherein R$_7$ is hydrogen, C$_1$-C$_4$alkyl or phenyl;

R$_1$ and R$_2$, independently from each other, represent aliphatic or aromatic groups;

R$_3$ and R$_4$, independently from each other, represent aliphatic or aromatic groups;

R$_5$ and R$_6$ are each hydrogen or together represent with the carbon atoms to which they are bonded, a phenyl ring; which process comprises reacting a compound of formula II

[RuCl$_2$(R$_8$)n]m     (II), wherein n is 1 and m is >1 which represents a polymeric structure if R$_8$ is a molecule containing two alkene or alkyne moieties coordinating in an hapto-2 coordination mode to the metal;

or n is 4 and m is 1 if R$_8$ is a nitrogen, oxygen or sulfur containing molecule in which said nitrogen, oxygen or sulfur coordinate to the metal;

in the presence of an inert solvent which boiling point is from 112° C. to 165° C. with a compound of formula III

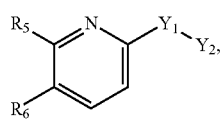
(III)

wherein R$_5$, R$_6$, Y$_1$ and Y$_2$ are as defined under formula I, and a phosphane of formula IV

R$_3$R$_4$P—X—PR$_1$R$_2$     (IV), wherein R$_1$, R$_2$, R$_3$, R$_4$ and X are as defined under formula I.

2. A process according to claim 1 for the preparation of a compound of formula I, wherein X is —CH$_2$—CH$_2$—CH$_2$—CH$_2$—.

3. A process according to claim 2 for the preparation of a compound of formula I, wherein R$_8$ is cyclooctadiene or bicyclo[2.2.1]hepta-2,5-diene if n is 1 and m >1; or is dimethylsulfoxide if n is 4 and m is 1.

4. A process according to claim 2 for the preparation of a compound of formula I, wherein R$_1$, R$_2$, R$_3$ and R$_4$ are phenyl and R$_5$ and R$_6$ are hydrogen or together represent with the carbon atoms to which they are bonded, a phenyl ring;

Y$_1$ is —CH$_2$—, and

Y$_2$ is NH$_2$.

5. A process according to claim 1, wherein the compound of formula III is represented by compounds from the group consisting of the formulae

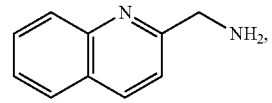
(III-2)

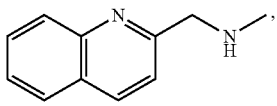
(III-4)

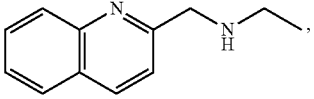
(III-6)

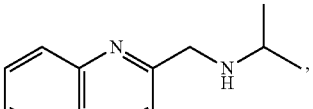
(III-8)

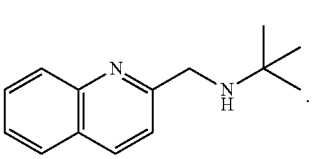
(III-10)

6. A process according to claim 1 performed as a one pot procedure.

7. A process according to claim 1 for the preparation of the compound of formula Ia

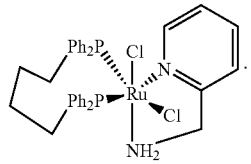
(Ia)

8. The compound of formula Ib

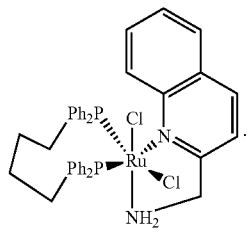
(Ib)

* * * * *